United States Patent [19]

De Burgh et al.

[11] Patent Number: 5,496,548
[45] Date of Patent: Mar. 5, 1996

[54] HUMAN ANTI-RH(D) MONOCLONAL ANTIBODIES, CELL LINES AND METHODS OF USE OF ANTIBODIES IN IMMUNOASSAYS

[75] Inventors: Benjamin A. De Burgh, Winterbourne Down; Alan Doyle, Salisbury; Belinda M. Kumpel, Congresbury, all of England

[73] Assignee: National Blood Authority, Watford, England

[21] Appl. No.: 45,244

[22] Filed: Apr. 13, 1993

Related U.S. Application Data

[63] Continuation of Ser. No. 469,517, Apr. 3, 1990, abandoned.

[30] Foreign Application Priority Data

Sep. 18, 1987 [GB] United Kingdom ............... 8722019

[51] Int. Cl.⁶ .................... A61K 39/395; C07K 16/34; C12N 5/22; G01N 33/53
[52] U.S. Cl. ................... 424/142.1; 424/153.1; 530/388.15; 530/388.7; 435/7.25; 435/240.27; 435/172.2; 435/70.21
[58] Field of Search ............... 530/388.15, 388.7; 424/85.8, 142.1, 153.1; 435/240.27, 172.2, 70.21, 7.25

[56] References Cited

PUBLICATIONS

Lomas et al., Transfusion 26:560, 1986.
Tippett, Medical Laboratory Sciences 45: 88–93, 1988.
Bron et al., PNAS USA 81:3214–3217 1984.
McCann et al. J. Immunological Mtds. 115(1):3–15 1988.
Thomson et al., The Lanlet 336:1147–1150, 1990.

*Primary Examiner*—Paula K. Hutzello
*Attorney, Agent, or Firm*—Burns, Doane, Swecker & Mathis

[57] ABSTRACT

The present invention provides human monoclonal antibodies having the following essential characteristics: (a) binding to Rh(D) antigen, but not C, c, E or e antigens of the Rh blood group system; (b) being IgG3 proteins; (c) having kappa light chains; (d) being of the allotype G3m(21); (e) binding to $D^u$ cells by an indirect antiglobulin test; (f) binding to $D^{IV}$, $D^V$ and $D^{VII}$ variant antigens; and (g) not binding to $D^{VI}$ or $D^B$ variant antigens, which may be employed for Rh-typing of red blood cells and passive immunization to prevent hemolytic disease of the newborn. Such a monoclonal antibody is exemplified by the monoclonal antibody of cell line ECACC 87091606 deposited at the European Collection of Animal Cell Cultures, Public Health Laboratory Service Center for Applied Microbiology and Research, Porton Down, Salisbury, Wiltshire, SP4, OJG, England of Sep. 16, 1987.

23 Claims, 2 Drawing Sheets

HUMAN ANTI-RH(D) MONOCLONAL ANTIBODIES, CELL LINES AND METHODS OF USE OF ANTIBODIES IN IMMUNOASSAYS

This application is a continuation of application Ser. No. 07/469,517, filed Apr. 3, 1990 and now abandoned, which was the national phase of International Application PCT/GB88/00756, filed Sep. 16, 1988.

The present invention relates to human monoclonal antibodies to the Rh(D) antigen of human red blood cells. In particular, it relates to such antibodies of the IgG3 sub-class which may be used to detect not only the normal Rh(D) antigen on either D-positive or "weak D" or $D^u$ cells, but also important variants of the Rh(D) antigen.

Of the antigens of the so-called Rh blood group system, the Rh(D) antigen is responsible for some of the most severe reactions following transfusion to a patient with corresponding antibody. Since an Rh(D−) individual with anti-Rh(D) who receives Rh(D+) blood is liable to suffer substantial red blood cell (RBC) destruction due to the Rh(D) phenotype incompatibility, blood of donors and blood transfusion recipients is routinely classified as Rh(D+) or Rh(D−) by agglutination tests with anti-Rh(D) antibody. The Rh phenotype of RBCs is commonly further defined with reference to the Fisher-Race system, which is based on the assumption that the inheritance of the Rh antigens is determined by three pairs of allelic genes, C-c, D-d and E-e, acting at very closely linked loci. According to this theory, a person may inherit a set of three Rh genes from each of his parents (i) C or c, (ii) D or d, (iii) E or e (no d antigen has as yet been identified, but the symbol 'd' is used to indicate the presence of a gene, allelic to the D gene, which does not produce D antigen). For example, an Rh(D+) person may inherit Cde from one parent and cde from the other. The frequencies of the commonest Rh gene combinations as determined with reference to the Fisher-Race system for an English population, together with the 'short symbols' which are used, particularly in speech, are given in Table 1 below.

TABLE I

Frequency of common Rh genes for an English Population

| Short symbol | CDE nomenclature | Frequency (%) |
|---|---|---|
| $R^1$ | CDe | 40.8 |
| r | cde | 38.9 |
| $R^2$ | cDE | 14.1 |
| $R^0$ | cDe | 2.6 |
| $R^{1w}$ | $C^wDe$ | 1.3 |
| r″ | cdE | 1.2 |
| r′ | Cde | 0.01 |
| $R^z$ | CDE | rarer |
| $r^y$ | CdE | rarer |
| $R^{=N}$ | (C)D(e) | rarer |

Despite expansion over the years, the Fisher-Race system has not been adequate to account for all the reactions that have been observed with the Rh system (Mollison, P. L. (1983) Blood Transfusion In Clinical Medicine, 7th edn., Blackwell Scientific, Oxford). Nevertheless, the World Health Organisation has recommended that in the interest of simplicity and uniformity this nomenclature should be universally adopted and all Rh genotypes given hereinafter are defined on the basis of the conventional Fisher-Race system.

In addition to the need for anti-Rh(D) antibody for Rh-typing of RBCs, such antibody is also importantly required for passive-immunisation of Rh(D−) mothers to prevent haemolytic disease of the newborn (HDN). This condition arises in newborn Rh(D+) infants of Rh(D−) mothers previously sensitized to Rh(D) antigen as a result of IgG anti-Rh(D) antibodies crossing the placenta during pregancy and causing foetal RBC destruction. Sensitization of the Rh(D−) mother to Rh(D) antigen may have occurred at the birth of an earlier Rh(D+) child due to some foetal RBCs entering the maternal circulation and being recognised by the maternal immune system. To reduce the incidence of HDN, it is routine practice in the United Kingdom and many other countries to give anti-Rh(D) antibodies to Rh(D−) mothers immediately after the birth of an Rh(D+) infant so that any Rh(D+) RBCs which have entered the maternal circulation are rapidly removed (Mollison, P. L. (1983) loc. cit.; Laros Jr., R. K. (1986), "Erythroblastosis Fetalis" in Blood Group Disorders in Pregnancy", Ch. 7, p. 103).

At the present time, anti-Rh(D) antibody for use in both Rh-typing of RBCs and passive immunisation of Rh(D−) mothers is largely obtained directly from female donors immunised during pregnancy or from immunised male volunteers. The success of the programme of post-partum prophylactic administration of human anti-Rh(D) immunoglobulin to Rh(D−) women has, however, resulted in a dramatic reduction in the number of naturally alloimmunised women (Urbaniak, S. J., "RhD haemolytic disease of the newborn: the changing scene", Br. Med. J. (1985) 291, 4–6). Also, deliberate immunisation of individuals with Rh (D+) RBCs carries the risks common to receiving any transfusion of RBCs, e.g. risk of transmission of hepatitis viruses and HIV. Hence, there is much interest in obtaining human monoclonal anti-Rh(D) antibodies for both diagnostic and therapeutic purposes.

As stated above, in routine blood testing, blood types are divided into Rh(D+) and Rh(D−) on the bases of the apparent presence or absence of Rh(D) antigen on the RBCs as indicated by agglutination tests with anti-Rh(D). However, a small number of persons with apparently Rh(D−) blood have RBCs that are not directly agglutinated by anti-Rh(D) during such routine testing, but that do react when the D-typing test is performed using selected anti-Rh(D) reagents by the indirect antiglobulin test. Cells thus identified are designated $D^u$. The frequency of the $D^u$ phenotype is about 0.2% overall, 0.6% among Caucasians, and about 1.5% of all Rh(D−) gravid women. At least three different mechanisms may be responsible for the expression of the $D^u$ phenotype: (1) hereditary absence of a portion of the complete Rh(D) antigen, (2) gene interaction with suppression of D by C in the trans position, and (3) a D gene producing a weak antigen.

In the early 1950s, reports first appeared of the presence of anti-Rh(D) in individuals of the $D^u$ phenotype following blood transfusion with Rh(D+) blood or pregnancy resulting in the birth of a Rh(D+) infant. It later became apparent that in some individuals whose blood is classified Rh(D+) parts of the Rh(D) antigen are missing from the RBCs. When exposed by transfusion or pregnancy to Rh(D+) RBCs carrying the complete Rh(D) antigen, persons carrying an incomplete Rh(D) antigen on their RBCs are capable of making alloanti-D against the Rh(D) antigen portion they lack. The blood of such individuals is called D variant when the RBCs react directly with routine anti-Rh(D) reagents or $D^u$ variant when the cells react only by the indirect antiglobulin technique.

The observation that allo anti-Rh(D) can be produced in patients who have Rh(D+) RBCs has led to common usage of the term "D mosaic" to describe the Rh(D) antigen in its complete native form. Routine anti-Rh(D) reagents generally cannot differentiate those RBCs that lack part of the D mosaic from those that have all the D components. The D variant phenotypes have been categorised by Tippett and Sanger (Vox. Sang. (1962)7, 9–13). This system is based on the interaction of RBCs and serum from D– and $D^u$ variant individuals. The six categories (see Table II below) allow for expansion; subdivisions are already recognised in categories III, IV and V. Categories I and II have been found to have so many similarities that they are now generally considered as a single sub-group.

TABLE II

Tippett and Sanger categories for D- or $D^u$ positive blood with anti-Rh(D)

| Category | Racial origin | Usual haplotype |
|---|---|---|
| I | White | DCe |
| II | | |
| IIIa | Black | |
| IIIb | Usually Black | Dce |
| IIIc | White | |
| IVa | Mostly Black, some White | |
| IVb | White | Dce |
| Va | Black and White | |
| Vb | White | $D^u$Ce |
| Vc | Black and white | |
| VI | Nearly all White | $D^u$Ce |

An alternative, but lesser used, classification by Wiener uses letters A, B, C, D instead of Roman Numerals. Although there is no direct correlation between the two systems, it is often considered that $D^B$ and $D^{VI}$ are interchangeable.

Although the frequency of D and $D^u$ variant individuals within the human population is relatively low, the total number of individuals of these blood types who potentially have some risk of effective anti-Rh(D) formation as a result of exposure by blood transfusion or pregnancy to non-varient Rh(D+) cells is far from insignificant. Morover, in addition to Rh(D–) women who give birth to Rh(D+) or $D^u$ infants, $D^u$ variant women who given birth to an Rh(D+) infant may also benefit from post-partum anti-Rh(D) treatment to reduce the risk of HDN (White, C. A. et al. (1983) Am. J. Obstet. Gynecol. 145,1069–1073). Anti-sera capable of distinguishing D and $D^u$ variant RBCs are not widely available. Hence, provision of anti-Rh(D) monoclonal antibodies with a range of binding specificities for D and $D^u$ variant RBCs is seen as useful in enabling the more ready identification and categorisation of individuals possessing such cells (especially D or $D^u$ variant pregnant females who are suitable candidates for prophylactic anti-Rh(D) treatment) as well as for providing further structural information on the Rh(D) antigen complex.

Human monoclonal anti-Rh(D) antibody production has previously been achieved by:

(a) directly cloning Epstein Barr virus transformed B lymphocyte cell lines (hereinafter referred to as EBV-transformed LCL) derived from B lymphocytes of anti-Rh(D) positive donors (see GB-A 2127434; Crawford et al. (1983) Lancet 1,386–388 and Paire et al (1986) Immunol. Lett. 13, 137–141), (b) cloning hybridoma cell lines formed by fusing anti-Rh(D) producing, EBV-transformed LCL with mouse, mouse-human or human myeloma cell lines (see copending British application no. 8709748, Thompson et al. (1986) Immunol. 58, 157–160 and EP-A-0162918), or (c) by fusion of a human LCL with immune B cells (Lowe et al (1986) Vox. Sang. 51, 212–216).

Figure 1:
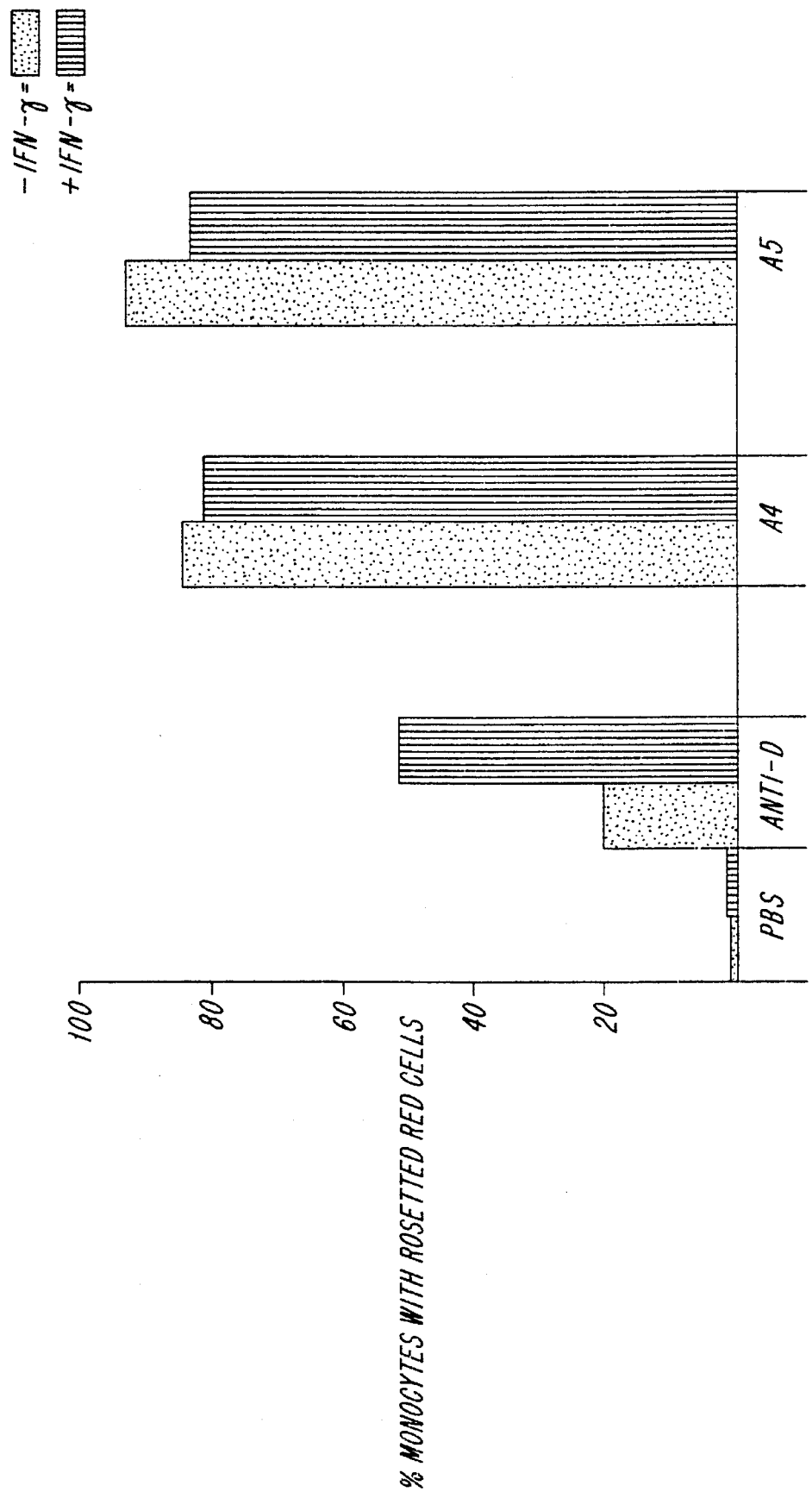
FIG. 1 is a comparison of phagocytosis results (expressed as the percentage of monocytes with one or more adherent or phagocyoed red cells) obtained with culture supernatants of clones A4 and A5 and a conventional polyclonal anti-Rh(D) serum.

By cloning EBV-transformed LCL from anti-RH9D) positive donors, we have been able to obtain, however, monoclonal anti-Rh(D) antibodies of the IgG class which have a particularly useful binding specificity spectrum not shown for any previously disclosed anti-Rh(D) monoclonal antibody reagent.

According to the present invention, we provide human monoclonal antibodies having the following essential characteristics:

(a) exhibiting activity against Rh(D) antigen, but not C, c, E or e antigens of the Rh blood group system;

(b) being IgG3 proteins;

(c) having kappa light chains;

(d) being of the alloytype G3m(21);

(e) exhibiting activity against $D^u$ cells by an indirect antiglobulin test;

(f) exhibiting activity against $D^{IV}$, $D^V$ and $D^{Tar}(D^{VII})$ variant antigens; and (g) being inactive against $D^{VI}$ or $D^B$ variant antigens, and antigen-binding fragments thereof.

In addition, monoclonal antibodies of the invention have been shown to exhibit activity against the $\overline{R}^N$ antigen.

Such monoclonal antibodies can be employed as routine anti-D reagents to classify RBCs as D-positive, $D^u$ or D-negative. For this purpose, a monoclonal antibody of the present invention may be employed either alone or in combination with one or more further anti- Rh(D) antibodies, preferably monoclonal antibodies having one or more additional binding specificities. Thus, for example, a monoclonal antibody of the present invention may be advantageously blended with a further monoclonal antibody capable of binding the $D^{VI}$ variant to provide an anti-Rh(D) reagent of broader specificity capable of classifying $D^{VI}$ variant RBCs as D-positive. In such an anti-Rh(D) reagent, an IgG1 antibody of the present invention may, for example, be combined with an IgG1 monoclonal antibody of the type disclosed in our copending International Application (WO89/02243) of even date herewith, which claims priority from GB-A 8722020 . having the following binding characteristics:

(a) exhibiting activity against Rh(D) antigen, but not C, c, E or e antigens of the Rh blood group system;

(b) exhibiting activity against $D^V$, $D^{Tar}$ ($D^{VII}$) $D^{VI}$ and $D^B$ variant antigens; and (c) being substantially non-reactive with non-papain treated $D^{IV}$ cells in an IAG test.

Amongst such antibodies, particularly preferred for use in combination with an anti-Rh(D) monoclonal antibody of the present invention is the monoclonal antibody designated B7 deposited at the European Collection of Animal Cell Cultures, Public Health Laboratory Service Center for Applied Microbiology and Research Porton Down, Salisbury, Wiltshire SP4 OJG, England under accession No. ECACC 87091603 on Sep. 16, 1987.

If monoclonal antibodies of the present invention are used for Rh-typing in parallel with an anti-Rh(D) reactive against $D^{VI}$ variants, e.g. an appropriate polyclonal anti-Rh(D) serum, those blood samples giving a positive result in an agglutination test with the latter, but negative results with a monoclonal antibody of the invention can be predicted to be mainly or entirely of the $D^{VI}$ category (since this is virtually the only D variant antigen against which the new monoclonal antibodies are inactive). It has been established that amongst individuals classified as Rh(D+) or $D^u$ by a conventional agglutination test, but who are capable of making anti-D, a high percentage have the $D^{VI}$ variant antigen (Mollison, P. L. (1983) in "Blood Transfusion In Clinical Medicine", Ch. 8, p 339). One use of the monoclonal antibodies of the invention is, indeed, in investigating the incidence of individuals of the $D^{VI}$ type in the population.

A monoclonal antibody of the present invention may also be of particular value for use in an anti-Rh(D) typing reagent to supplement the specificity of an anti-Rh(D) with no or only weak anti-$D^u$ activity, i.e. insufficient activity against $D^u$ cells to be able to reliably distinguish such cells to be able to reliably distinguish such cells from D-negative cells in a conventional agglutination test. Indeed, under FDA regulations in the U.S.A. governing commercial anti-Rh(D) typing reagents, it is obligatory for such a reagent to be able to distinguish $D^u$ RBCs from truly D-negative RBCs. Especially preferred amongst combination anti-Rh(D) reagents of the present invention are such reagents satisfying the above condition wherein an IgG anti-Rh(D) of the invention is employed together with an IgM anti-Rh(D) with no or only weak $D^u$ activity, e.g. an IgM monoclonal anti-Rh(D) selected from the monoclonal IgMs of the deposited hybridoma cell lines MAD-2 (cell line 86041803, deposited on Apr. 18, 1986 at the European Collection of Animal Cell Culture, Public Health Laboratory Service Center for Applied Microbiology and Research, Porton Down, Salisbury, Wiltshire SP4 OJG, England) and FOM-1 (cell line 87021301, deposited on Feb. 13, 1987 at the European Collection of Animal Cell Culture, Public Health Laboratory Service Center for Applied Microbiology and Research, Porton Down, Salisbury, Wiltshire SP4 OJG, England), which form inter alia, the subject matter of published European Patent Application 0251440. Such a reagent will advantageously be further complemented with at least one further IgG monoclonal anti-Rh(D) antibody which individually exhibits activity with $D^u$ red cells by the indirect antiglobulin test, such that the blended reagent reacts by the same test with $D^u$, $D^{IV}$, $D^V$ and $D^{VI}$ cells. When Rh typing is carried out with such a reagent, D-positive cells will firstly be directly agglutinated by the IgM anti-Rh(D). The remaining non-agglutinated cells (apparently D-negative) may then be subsequently divided into truly D-negative and $D^u$ cells by addition of conventional Coomb's reagent for an indirect antiglobulin test, whereupon $D^u$ cells binding IgG antibody will be agglutinated and thus distinguished.

The monoclonal anti-Rh(D) antibodies of the invention can be made by conventional methods known for the production of monoclonal antibodies and in particular by the culture of EBV-transformed human B-lymphocytes selected on the basis of secretion of anti-Rh(D) immunoglobulin having the characteristics set out above for the required antibodies. The culture supernatants so produced constitute a further feature of the present invention.

We have now investigated in detail 5 cloned EBV-transformed LCL which produce IgG3 anti-Rh(D) monoclonal antibodies as defined above, hereinafter referred to as A4, A5, A6, A7 and A8. All these cloned cell lines were obtained by starting with peripheral B lymphocytes from a chosen anti-Rh(D) donor and employing the procedure described in GB-A 2145113 or a substantially similar procedure to establish and clone EBV-transformed LCL producing a monoclonal antibody of the desired specificity (see Example 1). In continuous culture using RPMI-1640 medium supplemented with 10% (v/v) mycoplasma free-foetal calf serum, 0.2 mg/ml arginine and antibiotics to prevent mycoplasma growth, they have been found to be highly stable and to provide a culture supernatant having an anti-Rh(D) titre, as determined by an indirect antiglobulin (IAG) assay in low ionic strength saline versus $R_1R_1$ (CDe/CDe) RBCs, in the range 2000–16000. Such a culture supernatant is suitable for use in Rh-typing without the need for concentration and indeed, may be diluted for use.

Antibody production characteristics of the above-mentioned specific clones in continuous culture are summarised in Tables IIIa and IIIb below. All these clones have been shown to maintain a stable titre over at least 8 months continuous culture. The degree of agglutination in IAG tests was graded in conventional manner on a scale 0 to 6.

TABLE IIIa

| IAG titre (3% RBCs in low ionic strength saline) | |
|---|---|
| $R_1r$ cells | 64–256 |
| $R_1R_1$ cells | 2000–16000 |
| $R_1^u r$ cells Microtitre with bromelain-treated | 32–256 |
| $R_2R_2$ cells | 8000–16000 |
| Anti-Rh(D) (IU/ml) | 2–12 |
| IgG (μg/ml) | 1.1–2.8 |

TABLE IIIb

| culture supernatant | A4 | A5 | A6 | A7 | A8 |
|---|---|---|---|---|---|
| | IAG reactivity of supernatant with 3% RBCs in low ionic strength saline. (Grade: 0 to 6) | | | | |
| Red Cell Phenotype | | | | | |
| $R_1R_1$ | 6 | 6 | 6 | 6 | 5 |
| $R_1^u r$ | 6 | 6 | 5 | 5 | 5 |
| $R_0^u r$ | 6 | 6 | 6 | 6 | 5 |

It was further found that those monoclonal antibodies of the invention that were tested reacted with RBCs of phenotype $R_2rG$—, $hr^s$—, $R_1R_z$ and $R_2R_z$ but are negative with $r''Gr$, $r'''$, $r^G$, $r'^s r$, $hr^B$—, $r^w r$ and Rh33+.

According to a still further aspect of the present invention, we thus provide a method of Rh-typing of RBCs wherein an aqueous solution of a monoclonal anti-Rh(D) immunoglobulin of the present invention is employed. The monoclonal immunoglobulin is preferably contained in a culture supernatant which may be used directly or, more usually, after dilution. As hereinbefore indicated, it may be desirable to blend an IgG3 antibody of the present invention with one or more further anti-Rh(D) monoclonal antibodies of different specificity, e.g. a further IgG antibody having anti-$D^{VI}$ activity. Suitable diluents include physiological saline or phosphate buffered saline advantageously containing bovine serum albuin and a surfactant or suspending agent such as Tween 80 or methyl cellulose.

IgG3 anti-Rh(D) antibodies of the present invention are good promoters of binding and phagocytosis of Rh(D+) RBCs by monocytes and macrophages and hence are also of much interest from the point of view of providing effective prophylactic anti-D treatment for prevention of HDN. Indeed, culture supernatants of the cell lines A4 and A5 have been found in in vitro assays to induce greater rosetting and phagocytosis of sensitized RBCs by U937 monocytes than a conventional polyclonal anti-Rh(D) serum. Moreover, the same culture supernatants are comparable to a conventional polyclonal anti-Rh(D) serum in mediating binding of sensitized RBCs to cultured macrophages derived from interferon-γ stimulated monocytes. (see sections (iii) and (iv) of Example 1)

Thus, according to a further aspect of the present invention, we provide a monoclonal IgG3 antibody of the present invention for use in passive immunisation of an Rh(D−) or D or $D^u$ variant mother after the birth of an Rh(D+) child to prevent sensitisation of the mother to Rh(D) antigen. A sterile solution of such an antibody for human injection may be formulated in any physiologically acceptable aqueous medium, for example isotonic phosphate buffered saline or serum. Alternatively, the antibody may be supplied in a freeze-dried formulation read for reconstitution prior to use. To provide a highly effective prophylactic preparation for use in the prevention of HDN, a monoclonal anti-Rh(D) of the present invention may be employed with one or more further anti-RhD antibodies. For routine use, ideally an anti $D^{VI}$ antibody will be included. An antibody of the present invention may also find use in a prophylactic preparation to complement an IgG1 anti-Rh(D) monoclonal antibody our copending International Application (WO89/02442) of even data herewith, which claims priority from GB-A 8722018.

A7 of the above-mentioned cloned EBV-transformed lymphocyte cell lines was deposited on Sep. 16, 1987 at the European Collection of Animal Cell Cultures Public Health Laboratory Service Center for Applied Microbiology and Research, Porton Down, Salisbury, Wiltshire SP4 OJG, England under accession No. ECACC (call line 87091606).

Further details of the preparation of this deposited cell line and the identifying characteristics of its continuous culture supernatant are provided in Example 1 of the following non-limiting examples.

EXAMPLE 1

(i) Establishment and Cloning of Anti-Rh(D) Producing EBV-transformed LCL (a) Sources of B Lymphocytes Donor A: female, immunised during her first and only pregnancy (which resulted in delivery of a normal Rh(D+) infant), boosted with 0.5 ml packed Rh(D+) ($R_2r$) RBCs 4 years after parturition, and a peripheral blood sample obtained 8 days after boosting when her serum anti-D level was 60IU/ml.

(b) Establishment of cell lines

Peripheral blood mononuclear cells from donor A were separated on Lymphoprep (Myegaard and Co), incubated in the presence of EBV (1 ml culture supernatant from filtered mycoplasma free B95-8 cell line per $10^7$ cells) at 37° C. for 1 hour and washed in phosphate-buffered saline (PBS). Aliquots were plated at $0.5 \times 10^6$ cells/ml in 2 ml wells using lymphoblastoid cell culture medium (RPMI-1640 medium containing 10% (v/v) mycoplasma free foetal calf serum (FCS), 0.2 mg/ml arginine, 100 IU/ml penicillin (Glaxo), 50 µg/ml streptomycin (Glaxo), 25 IU/ml polymixin (Glaxo), 25 µg/ml kanamycin (Gibco), 20 µl/ml fungizone (Squibb), 25 µg/ml gentamycin sulphate (Sigma) and 20 µg/ml trobicin (UpJohn)), supplemented with either 1% (v/v) phytohaemagglutinin (PHA) or 0.5 µg/ml cyclosporin A (CsA), above a feeder layer of mouse periotoneal macrophages.

All the cultures were subsequently incubated at 37° C. in 5% $CO_2$, 95% humidified air. Medium changes were performed every 3 to 4 days and, after 3 weeks culture, the cells were transferred to 50 ml flasks. All the cell lines were enriched by rosetting at 3–4 weekly intervals.

(c) Cloning

Cells were plated out at limiting dilution at 5 and 10 cells per well in flat bottomed 96-well plates over a feeder layer of mouse periotoneal macrophages (Doyle et al. (1985) Human Immunology 13, 199–209). Cultures were fed once a week and after 3–4 weeks cloned cells positive for anti-D were grown up.

(d) Derivation of clones

The donor A polyclonal cell line giving rise to the clone A4 was initiated with PHA and sequentially enriched for anti-Rh(D) positive cells by rosetting 13 times before cloning.

Four further clones producing anti-Rh(D) antibody of the IgG3 sub-class (designated A5, A6, A7 and A8) were derived from lymphocytes from clone A4.

Clones A5, A6 and A7 were erroneously designated B4, B5 and B6 respectively in the priority application (GB-A8722019). The results of tissue type and karotype analysis of the above-selected cell lines are set out in Table IV below.

TABLE IV

| Cell Line | A5 A6 A7 A8 |
|---|---|
| Donor | A |
| sex | Female |
| Tissue Type | |
| HLA: A | 2,w19 |
| B | 44,35 |
| DR | 3,5 |
| Karotype | |
| sex chromosomes | xx |
| ploidy | some diploid cells, some tetraploid cells |
| markers | $12p^+, 22p^+$ |

(e) Quantitation of anti-Rh(D) activity and IgG in culture supernatants

Anti-Rh(D) activity in the supernatants was quantified against British national standards by Auto Analyser. The mean of at least two determinations was calculated. The quantitative estimation of IgG was performed by ELISA (modification of the method of Wakefield et al. in Clin. Chim. Acta. (1982) 123, 303–310) with at least eight determinations for each supernatant. Coating antibody (affinity purified goat anti-humna IgG (Sigma)) was used at 1/200 in 0.05M carbonate buffer pH 9.6. Supernatants and standard (purified human IgG (Sigma)) were diluted in RPMI 1640+ 10% FCS. Peroxidase-conjugated goat anti-human IgG (Sigma) was diluted 1/500 in PBS+0.05% Tween 20 and the substrate was TMB (3,3', 5,5'-tetramethyl benzidine).

Not all the cell lines established under different experimental conditions showed stable antibody production. However, all the cell lines which were subsequently cloned had maintained high titres (over 1/33,000 by microtitre) of anti-Rh(D) for over 6 months. All clones from these cell lines were positive for anti-Rh(D) and maintained their titres throughout the duration of continuous culture (e.g. in the case of A4 for over 2 years). The doubling time was 3–7 days. The cells grew well in suspension culture with no loss of antibody production.

(f) Immunoglobulin class and subclass determination

An immunodot assay (McDougal et al. (1983) 63, 281–290) was used to determine the reaction of the monoclonal anti-Rh(D) antibodies absorbed to nitrocellulose with anti-IgG, anti-Igm, anti-kappa and anti-lambda antiserum (Serotec); positive reactions were detected with peroxidase-conjugated anti-sheep IgG (Serotec) followed by colour development with 4-chloro-1-naphthol. The IgG subclass was evaluated by agglutination of anti-D coated RBCs by monoclonal anti-subclass antibodies (Unipath).

(g) SDS-Page and Western Blotting

Iscove's supernatants (serum free) were electrophoresed under reducing conditions on 15% polyacrylamide gels (Laemmli, Nature (1970) 227, 680–685). The separated proteins were then electrophoretically transferred to nitrocellulose membranes (Brunette, Annals Biochem. (1981) 112, 195–203), which were probed with anti-IgG antiserum (Serotec) and detected as above.

The monoclonal antibodies of the cell lines A4, A5, A6 and A7 were all found to have a heavy chain of molecular weight approximately 61,000 Daltons.

(h) Protein A absorption 2 ml volumes of supernatants were run twice down a 25 mm (1 ml) column of Protein A sepharose C1-4B (Sigma) and absorption of anti-D assessed by titration. The anti-Rh(D)s of the selected cell lines were not absorbed by Protein A, as expected for immunoglobulins of the IgG3 subclass.

(g) Gm allotyping

RBCs were coated with the monoclonal anti-Rh(D) antibodies and agglutination assessed using panels of Gm allotyping reagents (Birmingham or Amsterdam).

(ii) Serology

Culture supernatants from continuous cultures of the selected cell lines were tested by the IAG test using rabbit anti-human IgG and using 3% $R_1R_1$, $R_1r R_1{}^u r$ or $R_o{}^u r$ cells in low ionic strength slaine (see Tables IIIa and IIIb). The same supernatants were also tested against a panel of D variant RBCs under the same conditions (see Table V below). The degree of agglutination was graded in conventional manner on a scale of 0 to 6.

TABLE V

Reaction of monoclonal anti-Rh(D) antibodies with "partial" D positive red cells using IAG

| Culture supernatant | A4 | A5 | A6 (Grade: 0 to 6) | A7 |
|---|---|---|---|---|
| $D^{IV}$ | 5 | 5 | 6 | 6 |
| $D^V$ | 5 | 5 | 6 | 6 |
| $D^{Tar}$ ($D^{VII}$) | 5 | 5 | 6 | 6 |
| $D^{VI}$ | 0 | 0 | 0 | 0 |
| $D^B$ | 0 | 0 | 0 | 0 |

(iii) U937 Monocyte rosetting and phagocytosis assay

100 μl packed $OR_1R_2$ RBCs were sensitised with 500 μl anti-D (previously adjusted to 1 μg/ml) at 37° for 60 minutes, washed and resuspended at 1×10⁸ cells/ml in RPMI. U937 cells were taken in the log phase of growth and cultured for two days either in the presence or absence of interferon-γ (Amersham) at 50 U/ml. 45×10⁶ red cells were then added to a pellet of 1.5×10⁶ U937 cells and mixed, giving a ratio of 30:1. For the rosetting asay, the cells were incubated at room temperature for 5 minutes, spun at 600 rpm for 3 minutes and examined in a haemocytometer after a further 5–20 minutes. Phagocytosis was assessed immediately after incubating the cells at 37° for 3 hours. Results were expressed as the percentage of monocytes with one or more adherent or phagocytosed red cells.

Figure 2:
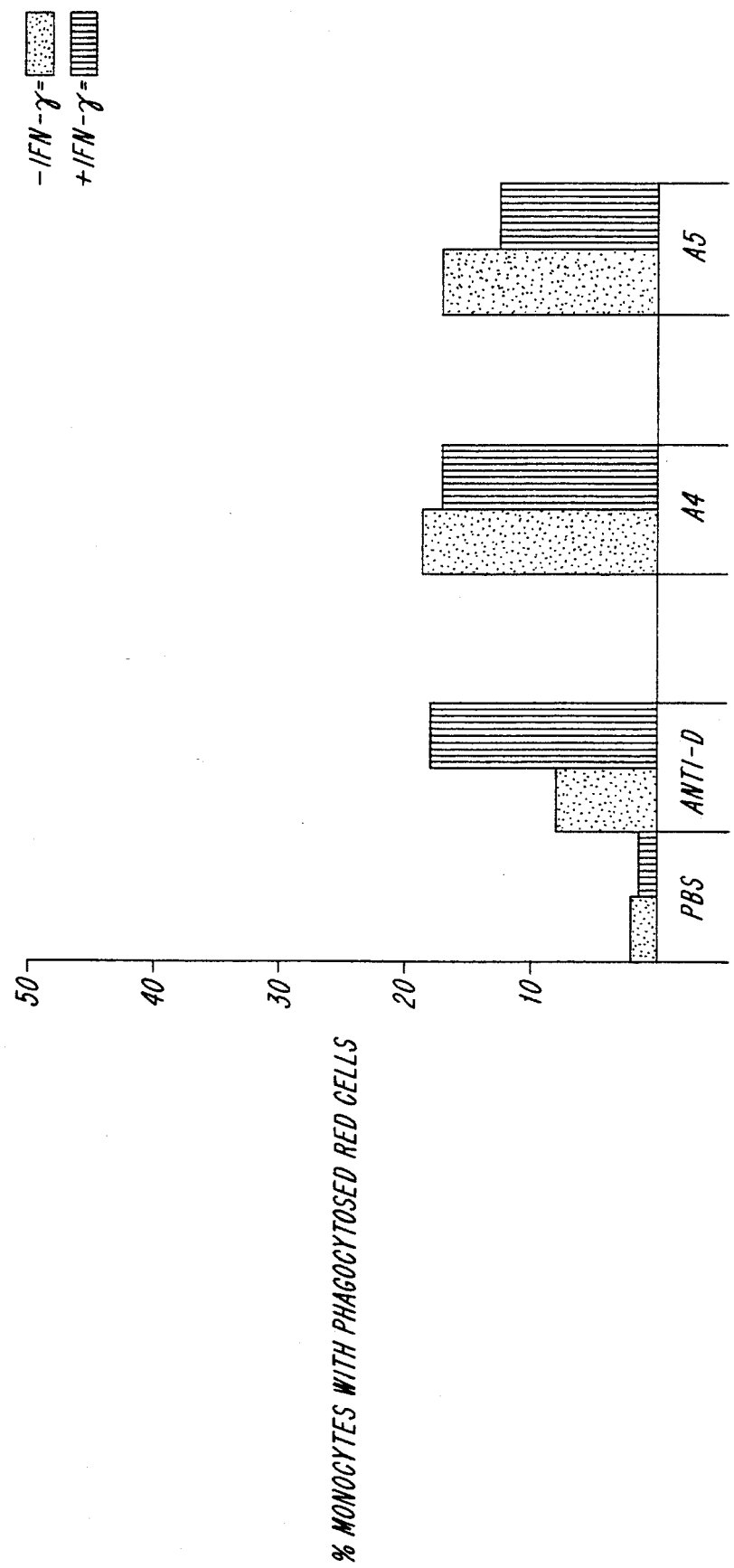
FIG. 2 is a comparison of phagocytosis results (expressed as the percentage of monocytes with one or more adherent or phagocytosed red cells) obtained with culture supernatants of clones A4 and A5 and a conventional polyclonal anti-Rh(D) serum.

A comparision of the results obtained with culture supernatants of clones A4 and A5 and a conventional polyclonal anti-Rh(D) serum is given in FIGS. 1 and 2. Red cells sensitised with culture supernatant from clone A8 formed rosettes with 100% of U937 cells (cultured in the absence of interferon-γ).

(iv) Macrophage binding assay

RBCs ($R_2r$) (1 volume) were sensitised with monoclonal anti-Rh(D) (2 volumes of untreated culture supernatant) and incubated with monocyte-derived cultured macrophages. The macrophages were stimulated with 500 U/ml of recombinant immune interferon (Biogen, Geneva) during the 48 hours prior to their use in the assay. The binding of RBCs to macrophages was assesed microscopically and expressed as the macrophage binding index (=number of red cells attached to or ingested by 100 macrophages).

Table VI below shows the results obtained with culture supernatants of clones A4 and A5. The ability of these supernatants to bring about red cell-macrophage interaction was similar to that of the polyclonal anti-Rh(D), which served as a positive control.

TABLE VI

| Source of anti-D | culture supernatant A4 | culture supernatant A5 | Polyclonal anti-Rh(D) serum |
|---|---|---|---|
| Macrophage binding index | 480 | 472 | 416–500 |
| anti-Rh(D)(IU/ml) | 2 | 12 | 43 |

(v) Lymphocyte ADCC assay

The culture supernatants of clones A4, A5, A7 and A8 were tested in a lymphocyte antibody-directed cell cytoxicity (ADCC) assay. Equal volumes (50 μl) of target cells (chromium-51 labelled $R_1R_1$ RBC suspension), effector cells (K lymphocytes) and anti-Rh(D) culture supernatant were incubated overnight at 37° C. in microplates after mild centrifugation and the chromium −51 release measured (Urbaniak (1979) Br. J. Haematol. 42, 303–314). The effector: target cell ratio was 15:1.

None of the culture supernatants tested were found to exhibit significant ADCC activity (see Table VII below).

TABLE VII

| Monoclonal antibody | A4 | A5 | A7 | A8 | Anti-Rh(D) serum. |
|---|---|---|---|---|---|
| % specific lysis. | | | | | |
| Effector KF | −2 | 1 | 0 | * | 95 |
| Effector BW | 4 | 0 | 0 | * | 92 |
| Effector TJ | * | * | * | 0 | * |

*not determined

We claim:

1. A human monoclonal antibody having the following essential characteristics:

(a) binding to Rh(D) antigen, but not C, c, E or e antigens of the Rh blood group system;

(b) being IgG3 proteins;

(c) having kappa light chains;

(d) being of the allotype G3m(21);

(e) binding to $D^u$ cells by the indirect antiglobulin test;

(f) binding to $D^{IV}$, $D^V$ and $D^{Tar}$ ($D^{VII}$) variant antigens; and (g) not binding to $D^{VI}$ or $D^B$ variant antigens; and antigen-binding fragments thereof.

2. The monoclonal antibody of claim 1 produced by the cell line ECACC 87091606.

3. A human lymphocyte-derived cell line which produces a monoclonal antibody as claimed in claim 1.

4. The cell line of claim 3 deposited at the European Collection of Animal Cell Cultures under accession No. ECACC 87091606.

5. An Anti-Rh(D) reagent comprising a monoclonal antibody as claimed in claim 1 in combination with one or more further anti-Rh(D) antibodies which bind to additional Rh(D) variant antigens.

6. An anti-Rh(D) reagent as claimed in claim 5 wherein a monoclonal antibody which binds the $D^{VI}$ variant antigen is present.

7. The anti-Rh(D) reagent as claimed in claim 5 wherein the one or more further anti-Rh(D) antibodies comprise an IgM anti-Rh(D) antibody with no binding activity to cells of the $D^u$ phenotype.

8. An anti-Rh(D) reagent as claimed in claim 7 wherein the IgM anti-Rh(D) antibody is selected from the group consisting of the monoclonal IgMs produced by the deposited hybridoma cell lines MAD-2 (ECACC 86041803) and FOM-1 (ECACC 87021301).

9. The anti-Rh(D) reagent as claimed in claim 7, further comprising an IgG monoclonal anti-Rh(D) antibody which binds to $D^{VI}$ red cells.

10. An anti-Rh(D) reagent comprising a monoclonal antibody as claimed in claim 2 in combination with one or more further anti-Rh(D) antibodies which bind to additional Rh(D) variant antigens.

11. An anti-Rh(D) reagent as claimed in claim 10 wherein a monoclonal antibody which binds the $D^{VI}$ variant antigen is present.

12. The anti-Rh(D) reagent as claimed in claim 10 wherein the one or more further anti-Rh(D) antibodies comprise an IgM anti-Rh(D) antibody with no binding activity to cells of the $D^u$ phenotype.

13. The anti-Rh(D) reagent as claimed in claim 12 wherein the one or more further anti-Rh(D) antibodies are selected from the group consisting of the monoclonal IgMs produced by the deposited hybridoma cell lines MAD-2 (ECACC 86041803) and FOM-1 (ECACC 87021301).

14. The anti-Rh(D) reagent as claimed in claim 12, further comprising an IgG monoclonal anti-Rh(D) antibody which binds to $D^{VI}$ red cells.

15. A monoclonal antibody as claimed in claim 14 for use in passive immunisation to prevent haemolytic disease of the newborn.

16. A pharmaceutical composition for use in passive immunisation to prevent haemolytic disease of the newborn comprising a monoclonal antibody as claimed in claim 14 or 15 in association with a physiologically acceptable carrier or diluent.

17. A pharmaceutical composition as claimed in claim 16 which further comprises a monoclonal antibody which binds the $D^{VI}$ variant antigen.

18. A method of Rh-typing for detection of the Rh(D) antigen on human red blood cells, said method comprising the following steps:

(a) contacting human red blood cells with a monoclonal antibody as claimed in claim 14 or claim 15, whereby binding of said antibody to any Rh(D) antigens present on the cell surface is achieved, thereby permitting agglutination of said cells;

(b) detecting whether or not said agglutination occurs; and (c) correlating said agglutination to the presence of the Rh(D) antigen.

19. A method of Rh-typing as claimed in claim 18 wherein said monoclonal antibody is in the form of an aqueous solution.

20. A method of Rh-typing for detecting the Rh(D) antigen on human red blood cells, comprising the following steps:

(a) contacting human red blood cells with an anti-Rh(D) reagent as claimed in any one of claims 7 or 16–19, whereby binding of said reagent to any Rh(D) antigen present on the cell surface is achieved, thereby permitting agglutination of said cells;

(b) detecting whether or not said agglutination occurs; and (c) correlating said agglutination to the presence of the Rh(D) antigen.

21. A method of Rh-typing as claimed in claim 20 wherein said reagent is in the form of an aqueous solution.

22. A composition comprising a monoclonal antibody as claimed in claim 1 and an anti-Rh(D) monoclonal antibody of the IgG1 sub-class.

23. A culture supernatant obtained by cultivation of a cell line as claimed in claim 3 or claim 20.

* * * * *